United States Patent [19]
Staples et al.

[11] Patent Number: 6,045,758
[45] Date of Patent: Apr. 4, 2000

[54] TEST SAMPLE CARD WITH CORED FEATURES

[75] Inventors: John Staples, Florissant; Garry Tegeler, Hazelwood, both of Mo.; Raymond O'Bear, Granite City, Ill.

[73] Assignee: bioMérieux, Inc., Hazelwood, Mo.

[21] Appl. No.: 08/852,755

[22] Filed: May 7, 1997

Related U.S. Application Data

[60] Division of application No. 08/587,633, Jan. 17, 1996, Pat. No. 5,766,553, which is a continuation-in-part of application No. 08/455,534, May 31, 1995, Pat. No. 5,609,828.

[51] Int. Cl.$^7$ .................................................. C12M 1/18
[52] U.S. Cl. ........................................ 422/102; 435/288.4
[58] Field of Search ............................. 422/99, 101, 102, 422/103; 435/288.4

[56] References Cited

U.S. PATENT DOCUMENTS

| | | |
|---|---|---|
| D. 243,542 | 3/1977 | Fadler et al. . |
| D. 243,543 | 3/1977 | Fadler et al. . |
| D. 254,687 | 4/1980 | Fadler et al. . |
| 3,880,978 | 4/1975 | Apostoleris et al. . |
| 3,957,583 | 5/1976 | Gibson et al. . |
| 3,963,355 | 6/1976 | Aldridge et al. . |
| 4,018,652 | 4/1977 | Lanham et al. . |
| 4,038,151 | 7/1977 | Fadler et al. . |
| 4,074,940 | 2/1978 | Tarbet . |
| 4,116,775 | 9/1978 | Charles et al. . |
| 4,118,280 | 10/1978 | Charles et al. . |
| 4,159,875 | 7/1979 | Hauser . |
| 4,260,687 | 4/1981 | Jacobson et al. . |
| 4,318,994 | 3/1982 | Meyer et al. . |
| 5,340,747 | 8/1994 | Eden . |
| 5,342,581 | 8/1994 | Sanadi . |
| 5,374,395 | 12/1994 | Robinson et al. . |
| 5,609,828 | 3/1997 | O'Bear et al. . |

FOREIGN PATENT DOCUMENTS

| | | |
|---|---|---|
| 0282840 | 9/1988 | European Pat. Off. . |
| 0526222 | 2/1992 | European Pat. Off. . |
| 0703052 | 3/1996 | European Pat. Off. . |
| 0745856 | 12/1996 | European Pat. Off. . |
| 2350593 | 12/1977 | France . |
| 2368774 | 5/1978 | France . |
| 9418369 | 8/1994 | WIPO . |

OTHER PUBLICATIONS bioMérieux Vitek, Inc. brochure "The Vitek 45 Well Test Card" (1994).
45–Well Card of bioMérieux Vitek, Inc. (1994).
Glenn Beall, Design Engineering, *Plastic Part Design for Economical Injection Moulding, Part 3–Incorporating Holes & Bosses*, Sep., 1985.
European Search Report for Appl. No. 96303456.6–2116/ dated Aug. 8, 1997.
European Search Report for Appl. No. 96303456.6 dated Nov. 7, 1997.

*Primary Examiner*—Lyle A. Alexander
*Attorney, Agent, or Firm*—McDonnell Boehnen Hulbert & Berghoff

[57] ABSTRACT

A test sample card has a fluid passage network provided on both sides of the card to provide for maximum separation distance between adjacent growth wells. The card also has cored sections along its periphery adjacent the wells, which improve the flow of plastic during the molding of the cards. The cored sections control the formation of knit lines in the surface of the card and eliminate knit lines from forming that could potentially bridge adjacent wells. These features, singly and together, combine to produce a card that is essentially immune to cross-talk between adjacent wells, yet permit a greater number of wells in a card of given dimensions. Improved bubble trap features are also provided for the card, including a bubble trap passage having a restriction formed therein. The restriction prevents air bubbles in the bubble trap from migrating back to the growth wells.

11 Claims, 5 Drawing Sheets

TEST SAMPLE CARD WITH CORED FEATURES

This is a divisional of application Ser. No. 08/587,633, filed Jan. 17, 1996, U.S. Pat. No. 5,766,553 which is a CIP of 08/455,534, filed May 31, 1995, now U.S. Pat. No. 5,609,328.

BACKGROUND OF THE INVENTION

A. Field of the Invention

This invention relates to the field of test sample cards and similar devices that hold samples for analysis by an optical system. Such sample cards are typically employed in chemical or biological sample testing systems.

B. Description of Related Art

Test sample cards typically have a plurality of small sample growth or reaction wells that are arranged in various arrays. The cards also have a fluid passage network that connects the growth wells to a fluid intake port. During manufacture of the card, one side of the card is taped with a clear adhesive tape to seal off one side of the wells. The individual wells are then loaded with a small quantity of chemicals or reagents, such as various growth media for bacteria, or various concentrations of different antibiotics or other drugs. After the growth wells are loaded with the chemicals, the other side of the card is sealed by a clear adhesive tape, sealing the other side of the wells.

When the cards are to be put in use, the wells of the card are loaded with the sample, for example a fluid containing a biological sample from a patient. The loading of the wells may be achieved by inserting one end of a straw-like transfer tube into the fluid intake port, and placing the other end of the transfer tube into a test tube containing the sample, thereby placing the fluid intake port in fluid communication with the sample. The test tube and card/transfer tube assembly is then placed in a vacuum chamber. Vacuum is applied to the chamber and then the chamber is vented to atmosphere. The venting process causes the fluid in the test tube to enter the intake port and travel along the fluid passage network to the growth wells.

Typically, the cards are provided with a bubble trap connected to the sample well. The user orients the card such that the bubble trap is positioned above the sample well and then gives the card a light tap, causing any air bubbles in the well to move into the bubble trap.

In a microbiological testing application for the card, after the card is loaded with a sample the card is incubated for a period of time, and then read by an optical system. The optical system typically employs some form of transmittance light source that illuminates the wells of the card, and a detector arrangement that measures the transmittance of light through the wells. The amount of transmittance depends on the reaction between the sample and the growth media or drugs placed in the growth wells. The transmittance measurements for the wells of the card permits an identification of an unknown agent in the sample, or the susceptibility of the agent to different antibiotics or other drugs, or the detection of a test reaction product.

Test sample cards of the prior art include a 30-well sample card which is described in U.S. Pat. No. 4,318,994 to Meyer et al. Other patents relating to the general subject of test sample cards include the Aldridge et al. patent, U.S. Pat. No. 3,963,355; the Fadler et al. patent, U.S. Pat. No. 4,038,151; the Robinson et al. patent, U.S. Pat. No. 5,374,395; and the Charles et al. patents, U.S. Pat. Nos. 4,188,280 and 4,116, 775. The Charles et al. patents also describe a card reading system for the 30-well cards described in the Meyer et al. patent.

As microbiological science has advanced over the past few decades, scientists have been able to isolate greater numbers of bacteriological agents and design suitable growth media and antibiotics for these agents. This development has resulted in a need in the art for test sample cards that have a greater number of growth wells. This need applies to both identification and susceptibility types of cards. Ideally, such a redesigned card would have the same physical dimensions and external features as the earlier generation of cards, so as to permit the redesigned card to be read by existing optical reading machines.

Placing greater numbers of wells on a card with fixed dimensions is not a simple matter of adding more wells to the cards. Rather, adding more wells to the card has the potential of increasing the possibility of inter-well cross contamination, a phenomenon known in the art as "cross-talk". Cross contamination of samples or reagents between adjacent wells can give erroneous test results when the cards are read. For example, by simply adding more wells to the 30 well card described in the above Meyer et al. patent, interwell contamination can result. To understand the difficulty in achieving higher well counts in a card of fixed dimensions, the key issue of cross-contamination between wells and how that can affect the performance of test sample cards will be discussed in further detail.

By placing more wells on a given amount of space on the card, the wells are placed closer together. Since all the wells are indirectly in fluid communication with each other by the card's fluid channel network, cross-contamination can result from sample, growth media or reagents diffusing along the fluid channel network from one well to an adjacent well, given enough time. Some types of cards may require incubation times of up to 18 hours, which is enough time for cross-contamination to occur if the wells are too close together. Thus, increasing the number of wells in the card poses a challenge in avoiding this type of cross contamination.

In the present invention, the inventors have solved this problem by designing a fluid channel passage network that achieves a sufficient separation distance between adjacent wells (as measured along interconnecting fluid channels), while also achieving an increased areal density of wells in the card.

The inventors have also discovered that the cross-talk problem is to some extent determined by how the molten plastic flows in the card mold during the manufacture of the card. The inventors have discovered that cross-contamination can occur by virtue of the sample media travelling along very tiny fissures or cracks that can form in the surface of the cards. These cracks, known as "knit lines", are inevitably created when two flow paths of molten plastic material meet during the card molding process. The inventors have appreciated that cross-talk can be minimized by controlling the formation in the knit lines in such a manner that they are reduced in number, and that they are oriented in a direction that is least likely to result in knit lines bridging adjacent wells.

Thus, the present invention provides design features in a test sample card that substantially reduces, if not eliminates, the probability of inter-well contamination. These features include the above-described special fluid channel networks. The invention further provides new coring techniques to improve the flow of card material during manufacture and the consequent control or elimination of knit lines that can cause inter-well contamination. Thus, the invention achieves the unexpected result of obtaining a larger number of wells per given area than prior art cards, while actually reducing the risk of cross-contamination.

The inventive test sample card possesses additional advantages and improvements. As noted above, a major issue in the design of sample cards is how the card handles the situation where air bubbles are present in the growth wells. The presence of air bubbles may be due to less than perfect vacuum conditions when the cards are loaded with samples, or as a byproduct of chemical reactions and biological processes taking place when the card is incubated with samples in the wells. The air bubbles have a tendency to distort the transmittance measurements. The invention provides for improved bubble trap and sample well features that facilitate the removal of air bubbles from the sample well into the bubble trap, and preventing of the air bubble, once in the bubble trap, from reentering the growth well. These features substantially improve the reliability of the transmittance measurements.

These and other features and advantages of the invention will be more apparent from the following detailed description of the invention.

SUMMARY OF THE INVENTION

A test sample card is provided having a body made from a molded material, the body comprising a fluid entrance port and first and second end regions and first and second side regions. A plurality of growth or reaction wells are located in the card body between the first and second end regions and the first and second side regions. A fluid channel network connects the fluid entrance port to said growth wells. To improve the flow of the material during the molding process, cored regions are disposed in at least one of the first and second end regions or the first and second side regions. The cored regions improve the flow of the molded material during the manufacture of the card and inhibit or control the formation of knit lines in the surface of the card in a manner so as to reduce the likelihood of contamination between different wells in the card.

In a preferred embodiment, the cored region is disposed along one of the sides of the card below the identification area on the card, and includes a plurality of dam features directed towards the growth wells. The dam features help prevent the formation of knit lines in the row direction (i.e., the direction defined by the wells in a single row), which is the direction having the shortest separation distance between adjacent rows as measured along the surface of the card. Cored features may also be formed at the ends of the card and along both sides, again helping prevent the formation of knit lines in the surface of the card and controlling the knit lines such that they form in a manner unlikely to bridge adjacent wells.

In another aspect of the invention, the card has a fluid channel network linking the fluid intake port to the wells, comprising a first set of fluid channels disposed in the top surface of the card and a second set of fluid channels disposed in the bottom surface of the card. The first and second fluid channels supply fluid to multiple wells in every row of wells in the card. The fluid channels are arranged on the card so as to increase the separation distance between adjacent wells, as measured along the fluid channels, thereby reducing the risk of contamination between adjacent wells. In a preferred embodiment, the separation distance is greater than or equal to one inch in a card measuring roughly 3½ inches by 2¼ inches.

In yet another aspect of the invention, at least one of the wells has a bubble trap in communication with the well via a bubble trap passage. The bubble trap passage has a well end and a bubble trap end, wherein the width of the well end of the bubble trap passage is greater than the width of the bubble-trap end of the bubble trap passage. This funnel-shaped bubble trap passage promotes the collection of air bubbles in the bubble trap. At the intersection of the walls forming the bubble trap passage and the bubble trap, a restriction is formed in the bubble trap passage. The restriction, preferably in the shape of a sharp corner, prevents any air bubbles in the bubble trap from migrating from the bubble trap back into the growth well.

A further embodiment of the invention provides for raised rail features along the sides of the card, which facilitate the stacking of cards without scuffing of the adhesive tape covering the cards. The scuffing can interfere with the optical measurements, and if serious enough, could disturb the adhesive tape and increase the possibility of inter-well contamination.

An object of the invention is to provide a test sample card with a reduced probability of cross-talk from adjacent growth wells.

A further object of the invention is to provide card molding features which control knit lines and prevent them from forming in a manner that could contribute to cross-talk.

A further object of the invention is to provide a test sample card that has a bubble trap passage that facilitates the collection of bubbles in a bubble trap, and prevents the bubbles from leaving the bubble trap and reentering the growth wells.

BRIEF DESCRIPTION OF THE DRAWINGS

Presently preferred embodiments of the invention are depicted in the drawings, wherein like reference numerals refer to like elements in the various views, and wherein.

DETAILED DESCRIPTION OF THE PREFERRED EMBODIMENT

Figure 1:
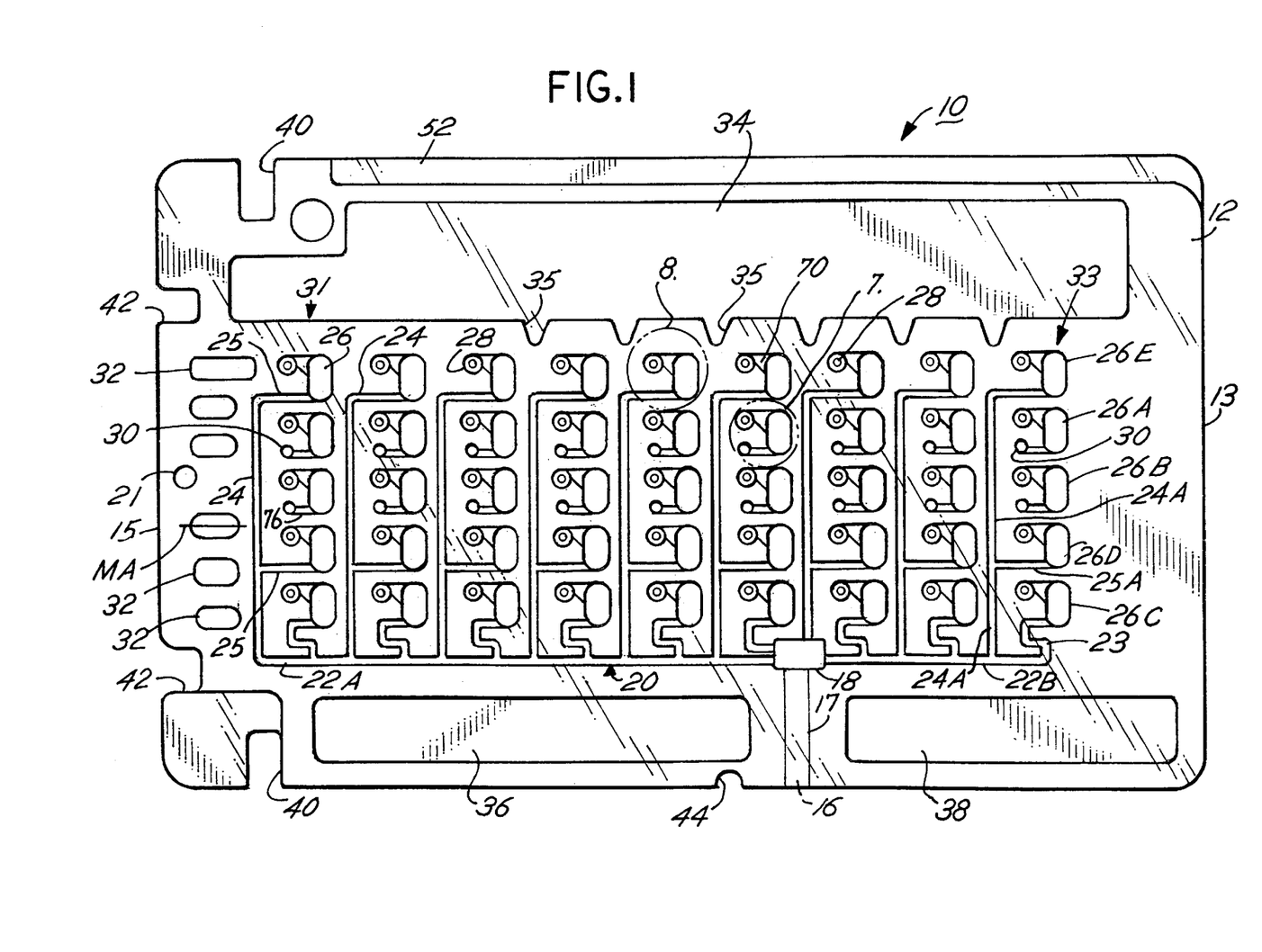
FIG. 1 is a plan view of the bottom side of the card.

FIG. 1 shows the bottom surface 12 of a preferred test sample card 10 in accordance with a preferred embodiment of the invention. The surface 12 is referred to as the "bottom" due to the fact that it receives clear adhesive tape first, and is placed face down during the loading of the wells with growth media or other chemicals or reagents. The card 10 has a rear edge 13, a front edge 15 and a top surface 14 shown in a plan view in FIG. 2. Preferably, the card 10 is manufactured using an injection molding process from crystal polystyrene, such as Dow Chemical Company Styron™ 666D crystal polystyrene, or the equivalent.

Figure 2:
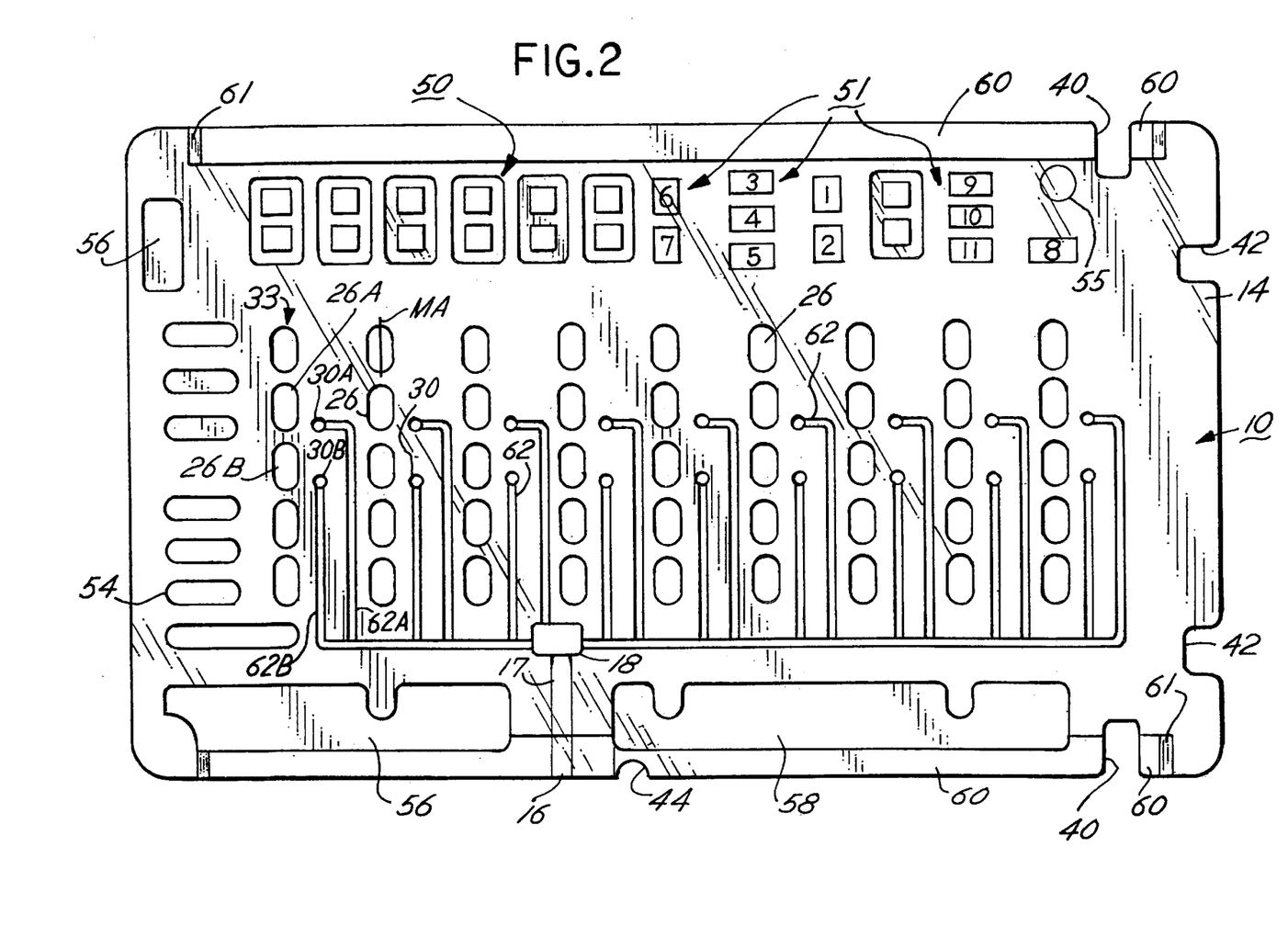
FIG. 2 is a plan view of the top side of the card.
Figure 4:
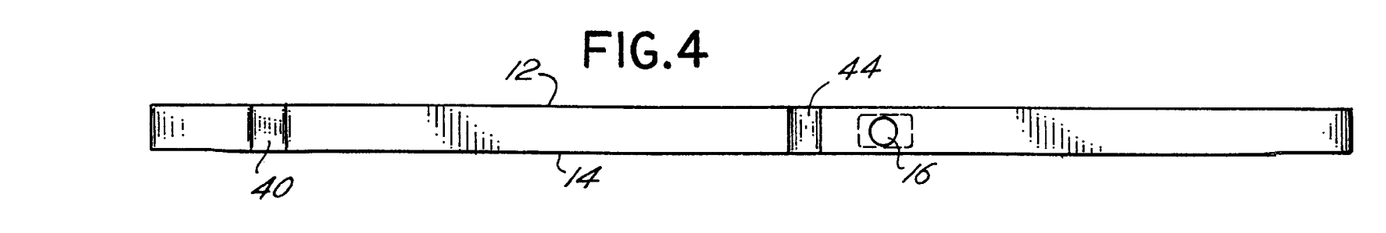
FIG. 4 is a side view of the card opposite to the side of FIG. 3.

Referring to FIGS. 1, 2 and 4, a fluid intake port 16 is located on the side of the card 10 which provides an opening for fluid containing biological or control or chemical samples to enter into the interior of the card 10. The port 16 is connected to a fluid intake passage 17 that leads to an intake manifold 18.

A fluid channel network 20 comprising a pattern of full-radius, shallow (e.g., 0.012 inches deep) grooves, is provided on the bottom surface 12. During the card loading process, fluid travels from the intake manifold 18 along the network 20 to a plurality of growth wells 26 arranged in an array in the card 10. The fluid passage network 20 includes primary fluid channels 22A and 22B extending horizontally to the left and right, respectively, of the manifold 18; a set of secondary fluid channels 24 extending upwardly from the fluid channels 22A and 22B; and a set of ternary fluid channels 25 which lead from the secondary channels 24 to the growth wells 26.

Each of the growth wells 26 contains a bubble trap 28 which is in communication with the growth wells 26 by a bubble trap passage 70. The bubble traps 28 and bubble trap passages 70 are discussed in detail in conjunction with FIGS. 7–12 below.

Figure 3:
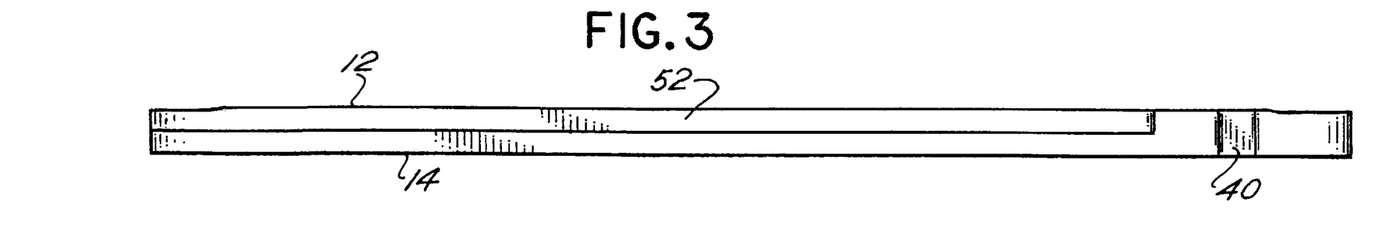
FIG. 3 is a side view of the card.
Figure 6:
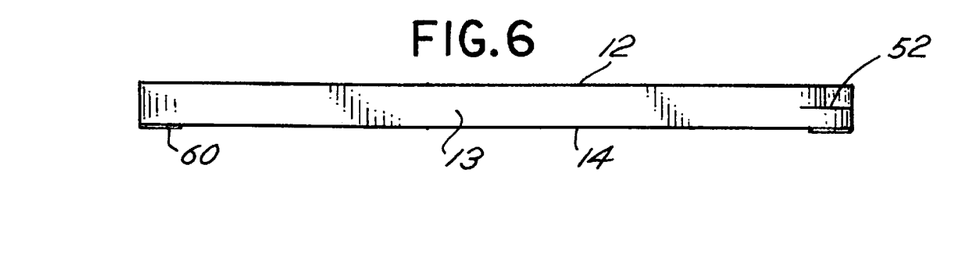
FIG. 6 is an end view showing the opposite end of FIG. 5.

As shown in FIGS. 1 and 6, the card 10 has a pair of opposed gripping slots 40 at the front end 15 of the card, which are gripped by mechanical structures in the card reader (not shown) for the card 10. Other gripping features could be provided for other types of readers. A pair of positioning notches 42 are provided in the front edge 15 of the card, which assist in the placement of the card 10 in proper alignment with the optical system for the card reader. A tray keeper notch 44 is provided along the side of the card 10 adjacent to the port 16. As shown in FIGS. 2, 3, and 6, an alignment groove 52 is provided on the bottom surface of the card to insure that the user correctly inserts the card in the reading machine. Alternative insertion and orientation features could of course be provided.

The top surface of the card 10 is shown in FIG. 2, and includes a second set of fill channel grooves 62 in communication with the manifold 18. The fill channels 62 each terminate in a through-card feed channel 30, which passes through the card 10 from the top side of the card shown in FIG. 2 to the bottom side of the card 10 shown in FIG. 1. The through-card feed channel 30 conducts fluid samples to a fill channel 76, shown in FIGS. 1 and 7. The fill channels 76 conduct sample fluid into the growth wells 26.

Figure 7:
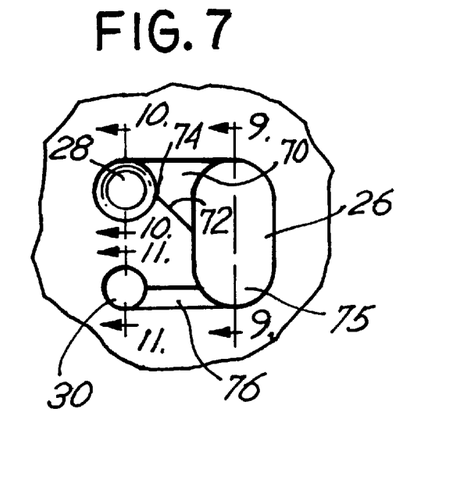
FIG. 7 is a detailed plan view of the wells of the card that receive fluid samples from the through-card feed channels of FIG. 2.

Referring now to FIG. 7, the growth wells 26 that receive fluid samples from the through-card feed channels 30 are shown in greater detail. The through-card feed channel 30 is shown in a vertical cross-sectional view in FIG. 11. The fluid sample passes through the card 10 from the top side of the card (FIG. 2) to the bottom side of the card (FIG. 1) via the throughcard feed channel 30, and then enters a fill channel 76. The fill channel 76 leads to the bottom portion 75 of the well 26.

From FIGS. 1 and 2, it can be seen that fluid channels are provided on both sides of the card 10. In particular, from FIGS. 1 and 2 it can be seen that the fluid channels on both sides of the card 10 provide an inter-well separation distance of at least one inch in a card with dimensions of approximately 3½ inches by 2¼ inches, with the inter-well separation distance measured along the fluid channels that connect the wells together. For example, referring to the left hand side of the top surface of the card (FIG. 2), fluid channel 62A provides a pathway for sample fluids to the growth well 26A via the through-card feed channel 30A. Well 26A is in communication with well 26B via channel 30A, fluid passages 62A and 62B, and channel 30B. By virtue of the elongate fluid channels 62A and 62B, the inter-well separation distance of wells 26A and 26B is on the order of an inch and half in the illustrated embodiment. The separation distance is sufficiently great that the probability of inter-well contamination along the passages 62A and 62B is exceedingly remote, even with a long incubation time for the card. For most microbiological applications, in which the sample remains in the wells for some time during incubation and reading, a minimum desirable separation distance as measured along the fluid channels is at least 0.75 inches, with at least one inch preferred. The greater the separation distance, the less likely that diffusion of fluids or reagents between wells along the fill channels will occur.

Referring to the right-hand side of FIG. 1, a potential cross-contamination pathway exists between wells 26C and 26D via fluid channels 23, 22B, 24A and 25A. However, the channels 23, 22B, 24A and 25A are designed such that the distance from well 26C to well 26D is greater than one inch, substantially reducing the possibility of inter-well contamination. The channel 23 is given an "S" shape to increase the distance from the channel 22B to the well 26C. Note further that well 26D has a potential cross-contamination pathway with well 26E via fluid channels 25A and 24A but this distance again is at least an inch in the illustrated embodiment, substantially eliminating the likelihood of inter-well contamination between wells 26E and 26D.

As can be seen from FIGS. 1 and 2, the wells 26 in the card are arranged in an array of multiple rows of wells 26, each of the rows of wells having a common fluid channel network described for the row 33 adjacent to the end 13 of the card.

As shown in FIG. 2, an identification area 50 is provided on the surface 14 of the card 10. The area 50 includes a series of "8"s which provide an area for a technician to write identification numbers associating the test sample card 10 with the particular patient or test. A card code block 51 is placed adjacent the area 50 and includes eleven identification blocks identifying the type of card depending on how the blocks are marked. An external test result (ETR) mark location 55 is also provided on the top surface.

Referring to FIG. 1, the card 10 further includes a first row 31 adjacent to end 15. A set of oval-shaped cored pockets 32 are provided having a major axis MA (FIG. 1) oriented towards the adjacent row 31 of wells 26. The molten plastic card material enters the mold at the molding gate region 21. The cored pockets 32 enhance the flow of the material during the molding of the cards 10. Specifically, the mold for the cards has positive elements that create the cored pockets 32 to help prevent the formation of knit lines adjacent to the first row 31 of wells 26 and prevent the formation of knit lines in the direction along the major axis MA (FIG. 2) of the wells 26 (i.e., the row direction where the separation distance between the wells measured along the surface of the card is the least). Referring to FIG. 2, a set of oval cored pockets 54 are also provided to reduce the possibility of knit lines being formed adjacent to the last row 33 of wells 26 in a manner parallel to the major axis of the wells. A preferred depth of the cored pockets 32 and 54 (height of the positive elements) is 0.07 inches, but this depth is not especially critical.

While oval shaped cored pockets are illustrated, other shapes could be used. Preferably, the shapes are either oblong or elongate with the long axis of the pocket oriented towards the adjacent row of wells, as shown in the example of oval pockets in FIGS. 1 and 2. This promotes a flow of molten plastic and control of knit lines such that the knit lines form, if at all, in a manner roughly parallel to the long axis of the pocket: the direction in which the inter-well separation distance as measured along the surface of the card is the greatest.

The side of the card 10 adjacent to the primary fluid channel 22A and 22B also contains cored sections 36 and 38. These cored sections control the formation of knit lines on the surface of the card 10 during the molding of the card, particularly in the vicinity adjacent to the first column of wells immediately adjacent to the primary fluid channels 22A and 22B.

Another cored section 34 is provided on the opposite side of the card as shown in FIG. 1, adjacent to the wells 26 in the far column of wells. The cored section 34 is preferably between 0.020 and 0.050 inches, so as to not interfere with the reading of the identification marks on the top surface of the card. A preferred depth of the cored section 34 is 0.030 inches. The cored section 34 is located on the bottom side of the card as shown in FIG. 1 directly behind the identification area 50, shown in FIG. 2. With a depth of 0.030 inches, the reading of the identification information in the regions 50, 51, 55 by an optical system in the card reader is not adversely affected.

The cored section 34 improves the flow of molten plastic material over the card during the manufacture of the card, and controls the formation of knit lines in the surface of the card. As shown in FIG. 1, the cored section 34 preferably includes a set of V-shaped dam portions 35 which improve the flow of the material during the molding of the card 10. The dam portions 35 (comprising extensions of the cored section 24 with a recess of, for example 0.03 inches) prevent knit lines from forming in a direction parallel to the major axis of the wells 26, where the separation distance (as measured along the surface of the card) is the least. Instead, the knit lines form, if at all, generally parallel to the minor axis of the wells, and thus are unlikely to bridge two wells.

In accordance with the above, persons of skill in the art of plastic molding will appreciate that the mold for manufacturing the test sample card has positive elements that create the recessed cored sections 32, 34, 54, 60 and the dam feature 35. For the cored sections 32, the positive elements comprise a set of an elongate oval elements positioned adjacent to the elements that define the rows of wells. The elongate elements have a major or long axis MA oriented perpendicular to the row direction. The positive elements direct the flow of card material in the mold during molding in a manner so as to control the formation of knit lines in the surface of the card.

Figure 13:
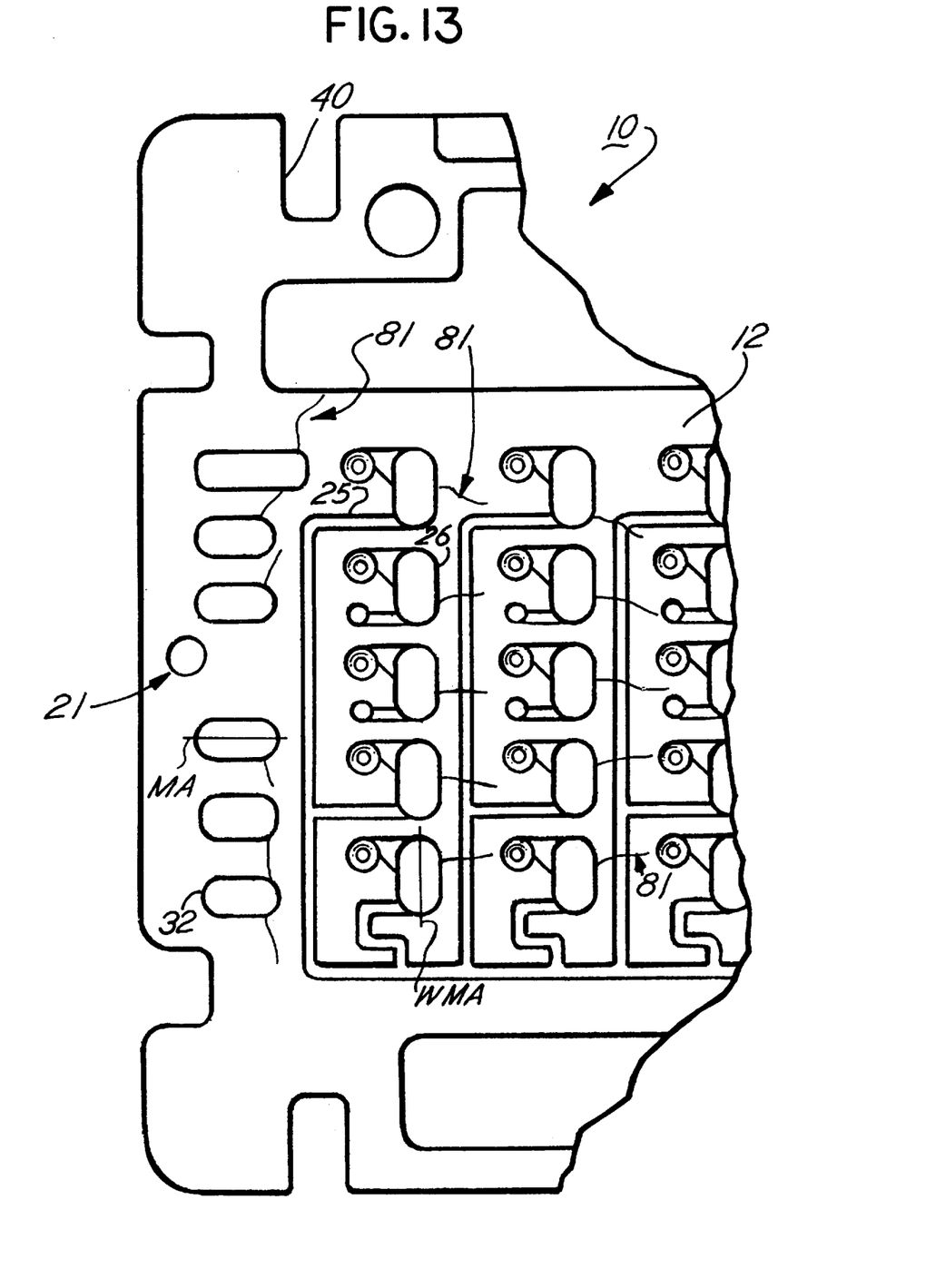
FIG. 13 is a plan view of a portion of the card shown greatly enlarged in order to illustrate how the cored sections control the formation of knit lines int he surface of the card.

Referring to FIG. 13, a portion of the bottom side 12 of the card 10 is shown enlarged in order to illustrate the how the cored sections control the formation of knit lines. The card material enters the mold at the gate 21. The knit lines 81 are tiny fissures (also exaggerated in thickness in FIG. 13) that form when plastic flows from the gate around the positive elements that form the cored sections 32. The flow of plastic in the mold is such that the knit lines 81 in the surface 12 of the card tend to form in a direction generally perpendicular to the well major axis MWA, which is the direction in which the inter-well separation distance (measured along the surface of the card) is the least. The same effect is achieved by the other cored sections in the card, including the dam features 35 in the cored section 34.

Figure 9:
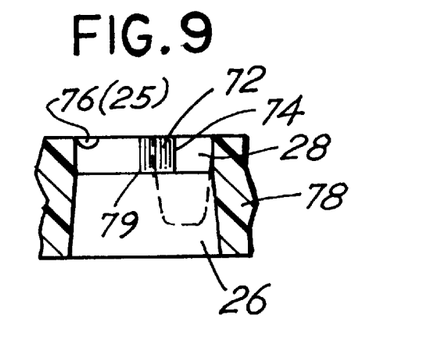
FIG. 9 is a sectional view of the wells along the lines 9—9 of FIGS. 7 and 8.

Referring to FIGS. 7 and 9, the card portion 78 surrounding the well 26 includes a slanted wall portion 72 that cooperates with wall 77 to form a generally funnel-shaped region in the bubble trap passage 70. The funnel-shape bubble trap passage 70 includes a restriction 74 comprising a sharp corner at the intersection of the bubble trap passage 70 and the bubble trap 28. In use, when the sample fluid enters the card and fills the well 26, the technician holds the card 10 in a position such that the bubble traps 28 are generally in an upward or vertically inclined position relative to the wells 26. The technician jiggles the card with a tap or a snap of the wrist, jiggling any air bubbles that may be present within the well 26 into the bubble trap 28. Taking advantage of the surface tension and meniscus properties of the sample fluid, the sharp corner restriction 74 serves to prevent any air bubbles that may be present in the bubble trap 28 from re-entering the well 26.

Figure 12:
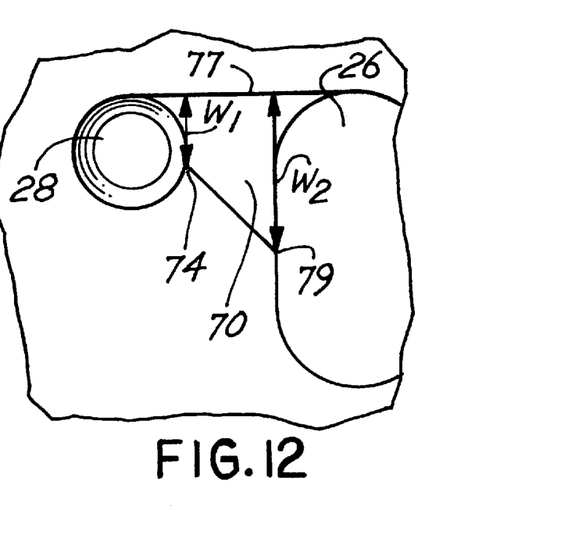
FIG. 12 is an enlarged plan view of the bubble trap passage showing the relationship between the dimensions of the entrance and restriction portions of the bubble trap passage.

The geometry of the bubble trap passage 70 is shown schematically in FIG. 12. At the intersection of the bubble trap passage 70 and the bubble trap 28, the width between the restriction 74 and the wall 77, W1, is less than 0.04 inches, with 0.033 inches in a preferred embodiment. At the entrance of the bubble trap passage, the width between the corner 79 and the wall 77, W2, is greater than W1 and 0.066 inches in the preferred embodiment. The relatively wide distance W2 allows air bubbles in the well 26 to be slinged into the bubble trap passage 70 and the bubble trap 28 when the card is tapped by the user. The narrow restriction at W1, and especially the sharp restriction corner 74, prevents the air bubble from migrating out of the bubble trap 28 and back into the well 26.

Figure 8:
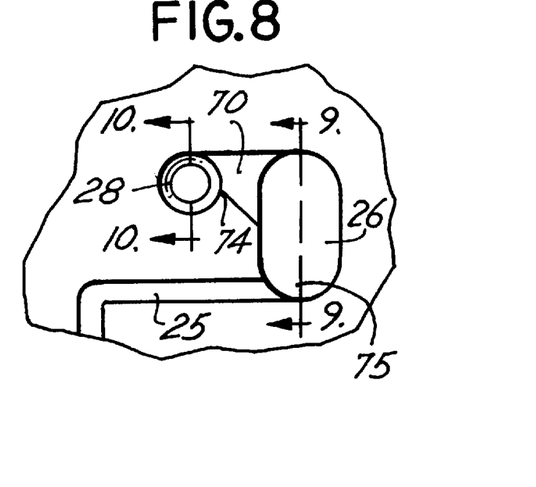
FIG. 8 is a detailed plan view of the wells of the card that receive sample fluid from the feed channels in the bottom surface of the card.
Figure 10:
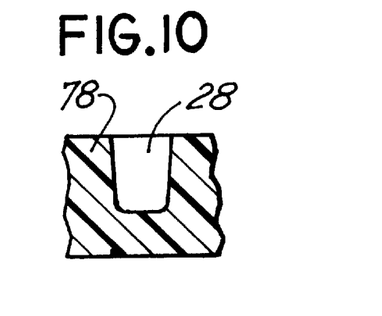
FIG. 10 is a sectional view of the bubble trap along the lines 10—10 of FIGS. 7 and 8.
Figure 11:
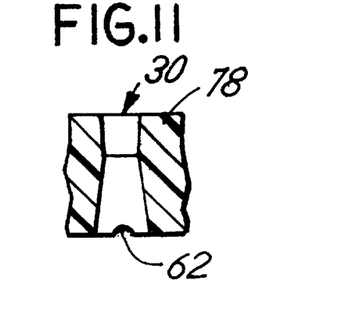
FIG. 11 is a sectional view along lines 11—11 of the through-card feed channel of FIG. 7.

Referring to FIG. 8, the construction of the wells that receive fluid samples along the fluid channels 25 is the same as that described in FIGS. 7 and 9. Referring to FIG. 10, the bubble trap 28 is shown in a sectional view along the lines 10—10 of FIGS. 7 and 8.

Figure 5:
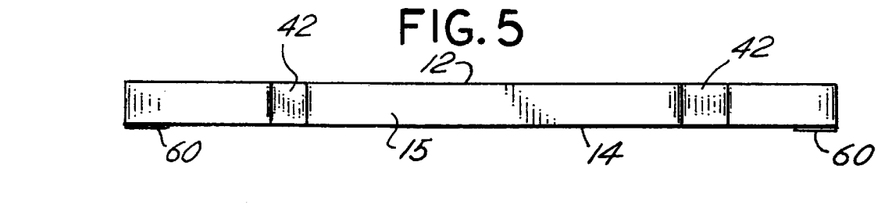
FIG. 5 is an end view of the card.

An additional feature to the card 28 is a rail feature that is used to separate cards from each other when the cards are stacked. This rail feature is especially useful when the cards are ejected from the mold and stacked on top of each other. The separation of the cards prevents any scuffing of the surface of the cards. After tape has been applied to the cards, the rails also prevent possible damage to the adhesive tape applied to the cards. Referring to FIGS. 2, 5 and 6, a pair of raised rail features 60 are provided on opposite edges of the card on one side of the card. The raised rail features 60 extend along substantially the entire length of the card 10. The height of the raised rails 60 need only be enough to prevent the adhesive tape covering the wells from touching when the cards are stacked. A height of 0.006 inches or thereabouts for the rail features 60 is sufficient for the illustrated embodiment. The ramp features 61 facilitate the stacking operation by allowing the rails to slide over each other as the cards are slid into a stacked condition.

Preferred sample loading and reading machines for the card are available from bioMérieux Vitek, Inc., 595 Anglum Drive, Hazelwood, Mo.

From the forgoing, it will be appreciated that some modification may be made from the preferred embodiment without departure from the true spirit and scope of the invention. For example, the location of the cored sections in the card may be modified somewhat depending on the particular material chosen from the card, the location of the wells, and the dimensions of the card. Further, the particular fluid channel design in the top and bottom surfaces of the card may be varied. For example, the channels could be designed in an alternating pattern, such that every other well in a row of wells receives fluid samples from fluid channels in the top and bottom surfaces of the card, thereby achieving an adequate inter-well separation distance. This true spirit and scope is defined by the appended claims, to be interpreted in light of the foregoing.

We claim:

1. A test sample card having a body made from a molded material, said body comprising a fluid entrance port and first and second end regions and first and second side regions, said body defining a plurality of wells placed between said first and second end regions and said first and second side regions, said body further comprising a fluid passage network connecting said fluid entrance port to said wells, the improvement comprising:

said body having cored regions comprising depressions in said body formed by positive elements in a mold forming said body, said cored regions disposed in at least one of said first and second end regions and said first and second side regions in a predetermined relationship to said wells so as to control the formation and direction of knit lines in the surface of said card relative to said wells, said cored regions improving the flow of said molded material during molding of said card in said mold to thereby control the formation of said knit lines in said material.

2. The sample card of claim 1, wherein said improvement further comprises cored regions disposed in at least one of said first and second end regions of said card.

3. The sample card of claim 2 wherein said wells are arranged in a plurality of parallel rows having a first row adjacent to said first end region and a last row adjacent to said second region, and wherein said cored regions comprise a first set of cored pockets oriented across said first end region substantially parallel and adjacent to said first row and a second set of cored pockets oriented substantially parallel and adjacent to said last row.

4. The sample card of claim 3, wherein said first and second cored pockets comprise elongate oval coring pockets defining a major axis arranged such that the major axis is oriented perpendicular to said first and last rows.

5. The sample card of claim 1 or claim 4, wherein said wells comprise 45 wells arranged in a plurality of parallel rows.

6. The sample card of claim 1, wherein said cored region comprises a cored area disposed in at least one of said first and second side regions.

7. The sample card of claim 6, wherein said cored area further comprises at least one dam portion disposed at the boundary of said cored region and the non-cored portion of said card.

8. The sample card of claim 6, wherein said card has a top surface and an identification region in said top surface and a bottom surface, said cored region in said bottom surface of said card below said identification region.

9. The sample card of claim 8, wherein said cored region has a depth of between 0.02 and 0.05 inches.

10. The sample card of claim 9, wherein said cored area as a depth of substantially 0.03 inches.

11. The sample card of claim 1, wherein said card is made from injection molded crystal polystyrene.

* * * * *